United States Patent [19]

Takezawa et al.

[11] Patent Number: 5,108,364
[45] Date of Patent: Apr. 28, 1992

[54] MONITORING CATHETER FOR MEDICAL USE

[75] Inventors: Jun Takezawa, Nagoya; Yasunobu Izumi, Yokohama; Mamoru Nishijima, Machida, all of Japan

[73] Assignee: Sumitomo Bakelte Company Limited, Tokyo, Japan

[21] Appl. No.: 479,700

[22] Filed: Feb. 15, 1990

[30] Foreign Application Priority Data

Feb. 16, 1989 [JP] Japan .................................. 1-35116
Nov. 21, 1989 [JP] Japan ................................. 1-300799

[51] Int. Cl.$^5$ .............................................. A61M 3/00
[52] U.S. Cl. ........................................ 604/43; 604/45; 604/53; 128/736; 128/748
[58] Field of Search ................. 128/673, 736, 748; 604/27, 43, 45, 53, 275, 276, 901

[56] References Cited

U.S. PATENT DOCUMENTS

| | | | |
|---|---|---|---|
| 3,951,136 | 4/1976 | Wall | 128/736 |
| 4,263,921 | 4/1981 | Trugillo | 128/736 |
| 4,497,324 | 2/1985 | Sullivan et al. | 128/736 |
| 4,603,699 | 8/1986 | Himpens | 128/673 |
| 4,717,379 | 1/1988 | Ekholmer | 604/43 |
| 4,721,115 | 1/1988 | Owens | 128/713 |
| 4,722,348 | 2/1988 | Ligtenberg et al. | 128/748 |
| 4,813,429 | 3/1989 | Eshel et al. | 128/736 |

FOREIGN PATENT DOCUMENTS 51-84181 7/1976 Japan .
139763 10/1981 Japan .
60-85730 5/1985 Japan .
60-99226 6/1985 Japan .

*Primary Examiner*—Stephen C. Pellegrino
*Assistant Examiner*—Michael Rafa
*Attorney, Agent, or Firm*—Browdy and Neimark

[57] ABSTRACT

A monitoring catheter for medical use characterized by a main tube for discharge path of body fluids, etc.; a first auxiliary tube for air flow which surrounds the main tube and is provided within the wall; a second auxiliary tube or a third auxiliary tube which forms passageway for liquid drug infusion or measures pressure; and a lead for measuring a temperature which is embedded within the wall of the main tube. The main tube has a plurality of bores on the wall near the tip portion thereof and also has a connecting portion for connecting with a container for drainage capture at the rear end of the main tube. The first auxiliary tube opens at the tip portion thereof towards the inside of the main tube and at the same time, is branched from the main tube near the rear end of the catheter and a filter is equipped at the rear end of the branched portion. The second auxiliary opens towards the outer surface of the catheter. The third auxiliary tube opens towards the outer surface of the catheter at a distance of 5 to 70 cm from the tip portion of the catheter. The tip of the lead is located near the tip portion of the catheter and is equipped with a temperature sensor. The lead is also branched from the main tube near the rear end of the catheter and the thus branched portion is equipped with a connector.

5 Claims, 4 Drawing Sheets

MONITORING CATHETER FOR MEDICAL USE

BACKGROUND OF THE INVENTION

Field of the Invention and Related Art Statement

The present invention relates to a monitoring catheter for medical use which is inserted into and maintained in to the esophagus or stomach to effect drainage or measure temperature or pressure, thereby to observe, monitor and control postoperative progress or the progress after treatment.

Catheters for measuring temperature in the esophagus or stomach have been used heretofore. No problem arises merely when a temperature is measured with a catheter but if the catheter is kept inserted in the body cavity, secretions might be congested to require discharge of the secretions. Also when other items for diagnosis, e.g., measurement of pressure, are required, an exclusive drain tube, a tube for measuring pressure, etc. should be inserted and kept stuck independently, and such results in complicated and troublesome handling. Furthermore, a plurality of tubes must be inserted into the body cavities, which leads to increased pains given to a patient.

To solve these problems, there are known catheters having multiple functions as shown in Japanese Patent Application Laid-Open Nos. 51-84181, 56-139763, 60-85730, etc. These catheters are all used by maintaining them in the esophagus and have functions to measure a body temperature and at the same time, monitor the heart sound, lung sound or electrocardiogram. However, these catheters lack functions of draining body fluids and infusing a liquid drug, or monitoring pressure, etc. On the other hand, with the catheter described in Japanese Patent Application Laid-Open No. 60-99226, a body temperature can be measured and at the same time, body fluids can be drained and a liquid drug can be infused but a pressure cannot be measured. Furthermore, since any auxiliary conduit for sampling is not equipped, it is difficult to perform smooth drainage. Thus, the catheters in the prior art involve problems that when they are maintained in a cavity such as esophagus, etc., congestion of secretions occurs and the congested secretions should be drained, although there is no problem with these conventional catheters in the case of measuring a single item with each of these catheters.

OBJECT AND SUMMARY OF THE INVENTION

In view of the forgoing circumstances, extensive investigations have been made to solve the problems involved in the prior art.

An object of the present invention is thus to provide a monitoring catheter for medical use which have multiple functions not only to measure a body temperature but also capable of measuring a pressure in any optional body cavity and further capable of effecting smooth drainage of secretions and if necessary, also performing drug infusion, washing, or applying to diagnosis or control of the function or condition of organs, etc. thereby to make control during operation or, observe, monitor or control the progress after operation or treatment in a simple Accordingly, the present invention relates to a monitoring catheter for medical use which is maintained mainly in the esophagus or stomach to effect drainage, measure a body temperature and measure a pressure, thus making control during operation or, observe, monitor or control the progress after operation or treatment.

Conventional catheters for measuring a temperature in esophagus, rectum, etc. do not have any function other than measuring the temperature, e.g., the function to drain body fluids. It is thus necessary to separately insert and retain a catheter tube for drainage, which results in a great deal of pain given to a patient. According to the present invention, drainage of body fluids can be facilitated with the catheter and for smooth drainage, a sampling function is further imparted to the catheter At the same time, there is also mounted a lumen capable of exclusively monitoring a pressure in the body cavity via the catheter. As the result, discharge of body fluids and if necessary and desired, infusion of a liquid drug or washing can also be effected by the catheter of the present invention.

Because of many such functions possessed by this single catheter, pains given to a patient can be minimized and handling of the catheter is also easy. Therefore, temperature control during, e.g., cardiac operation and postoperative temperature control in retaining the catheter contribute to keeping the condition of a patient stable also by the drainage function. Further by applying to respiration control, etc. due to measurement of a pressure, the catheter of the present invention can greatly contribute to postoperative observation, control and diagnosis.

DETAILED DESCRIPTION OF PREFERRED EMBODIMENTS

Figure 1A:
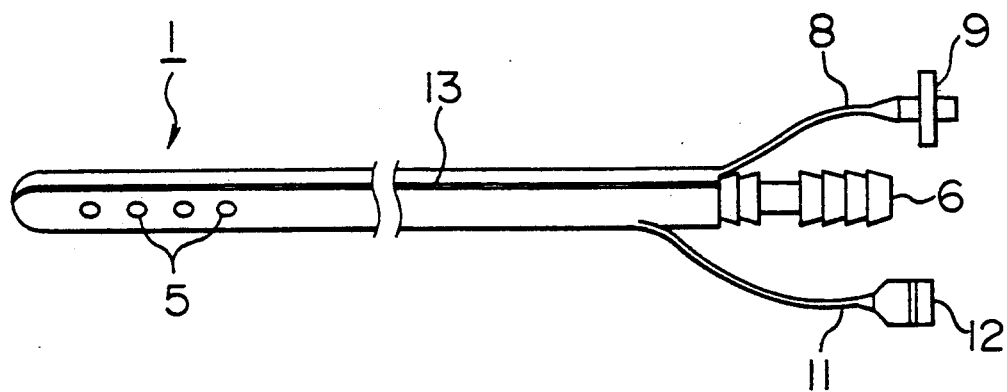
FIG. 1A shows one embodiment of the medical catheter which is one embodiment of the present invention.

The present invention relates to a monitoring catheter for medical use comprising a main tube for discharge path of body fluids, etc., a first auxiliary tube for air flow and a lead for measuring a temperature, the main tube having a plurality of bores on the wall near the tip, the first auxiliary tube being located within the wall of the main tube, the tip of the first auxiliary tube being open in the main tube, the lead being located within the wall of the main tube and a temperature sensor being mounted to the tip of the lead.

The main tube may also contain a connecting portion for connecting with a container for drainage capture at the rear end of said main tube.

The first auxiliary tube may be branched from the main tube near the rear end of the catheter. In case that the first auxiliary tube is branched, the rear end of the branched portion may have a filter.

The tip portion of the lead is preferably located near the tip of the main tube. The lead may also be branched from the main tube near the rear end of the catheter.

From a practical viewpoint, it is advantageous that the lead has a connecting portion at the rear end thereof.

The catheter may also be equipped with a second auxiliary tube which forms passageway for liquid drug infusion or for measuring a pressure. The second auxiliary tube is located within the wall of the main tube and opens towards the outer surface of the catheter for liquid drug infusion. The second auxiliary tube is preferably branched from the main tube near the rear end of the catheter The second auxiliary tube may further contain a connecting portion having a means for opening-closing at the rear end thereof.

The catheter may also have a third auxiliary tube which forms passageway for liquid drug infusion or for measuring pressure. The third auxiliary tube is located within the wall of the main tube and preferably has an opening toward the outer surface of the catheter at a distance of about 5 to about 70 cm apart from the tip portion of the catheter. The third auxiliary tube may be branched from the main tube near the rear end of the catheter. The third auxiliary tube may also have a connecting portion with a means for opening-closing at the rear end of the branched portion.

Hereafter the present invention is described in detail by referring to the drawings.

Figure 1B:
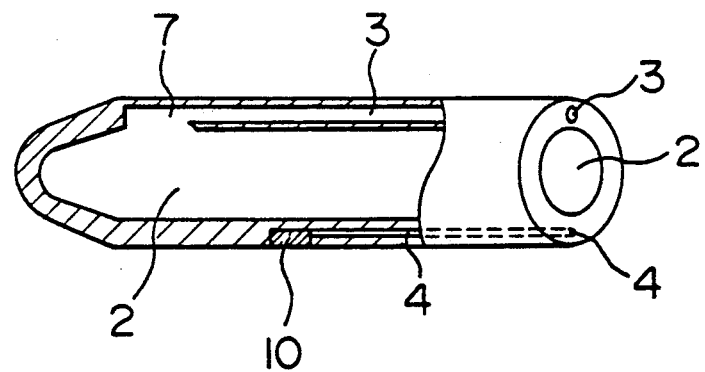
FIG. 1B is an enlarged and cross-sectional view of the tip portion shown in FIG. 1A.

FIGS. 1A and 1B show one embodiment of the present invention, having a drainage function with sampling and a temperature measuring function. This monitoring catheter 1 comprises main tube (2) having a hollow portion which forms a passageway for discharge liquid such as body fluids, etc., first auxiliary tube (3) provided within the wall of the main tube which surrounds the hollow portion of the main tube (2) and forms passageway of air flow, and lead (4) for measuring a temperature which is embedded in the wall of the main tube 3 apart from the first auxiliary tube. The monitoring catheter 1 has a plurality of bores (5) near the tip portion of the main tube (2). The tip portion of the main tube may be sealed and closed with the wall as illustrated in FIG. 1a. Alternatively, the tip portion may be opened, if necessary and desired (not shown). It is convenient that the rear end may have connecting portion (6) for connecting a container for drainage capture.

A thickness of the main tube wall which forms the hollow portion of the main tube (2) may be thick enough to provide the first auxiliary tube (3) and the lead (4) within the wall. Needless to say, the thickness should be sufficient to maintain the strength as the catheter.

The first auxiliary tube (3) opens at the tip portion towards the inner surface of the main tube (2) and is branched from the main tube near the rear end of the body of the catheter 1. At the rear end of branched tube (8), filter (9) is mounted. The inside of the main tube (2) is thus connected with the air via the first auxiliary tube (3) and the filter (9) so that the air which is not contaminated with bacteria, etc. flows through the first auxiliary tube (3) in spontaneous drainage and sucked drainage, whereby negative pressure in the main tube (2) of the catheter (1) kept inserted into a body cavity is weakened to prevent reduction in discharge efficiency due to adsorption of the catheter 1 to the viscous membrane or to prevent damages of the viscous membrane due to the adsorption, leading to smooth drainage. Where there is no danger of contamination at the region in which the catheter is inserted, it is not always necessary to provide the filter (9).

A plurality of the first auxiliary tubes (3) may also be provided.

The tip portion of the lead (4) is located near the tip portion of the body of the catheter (1) and temperature sensor (10) is mounted to the tip portion thereof so as to measure temperature at a specific area of the body cavity. The branched tube (11) at the rear end of the body of the catheter (1) is equipped with connector (12). By connecting with a monitoring portion, the temperature can be displayed and recorded. Examples of the temperature sensor include a thermocouple, a thermistor, a temperature-measuring platinum resistor, etc. but the temperature sensor is not deemed to be limited thereto. In view of cost, workability, etc., a thermocouple or a thermistor is preferred.

For embedding the lead (4), the lead (4) may be inserted into a hole previously provided in the wall of the catheter (1). Alternatively, the lead may be coated and embedded at the same time when the catheter tube is formed.

It is not always necessary to locate the temperature sensor (10) near the rear end of the catheter (1). The temperature sensor (10) may also be located on the way of catheter (1). It is also possible to provide a plurality of lead (4) and simultaneously measure temperatures at a plurality of regions.

From viewpoints of handling and assembling, it is advantageous that the body of the catheter (1) be integrally constructed with a soft plastic, rubber, etc. It is also advantageous that X ray contrasting line (13) be provided over the entire length of the tube for easy permeation with X rays.

Figure 2A:
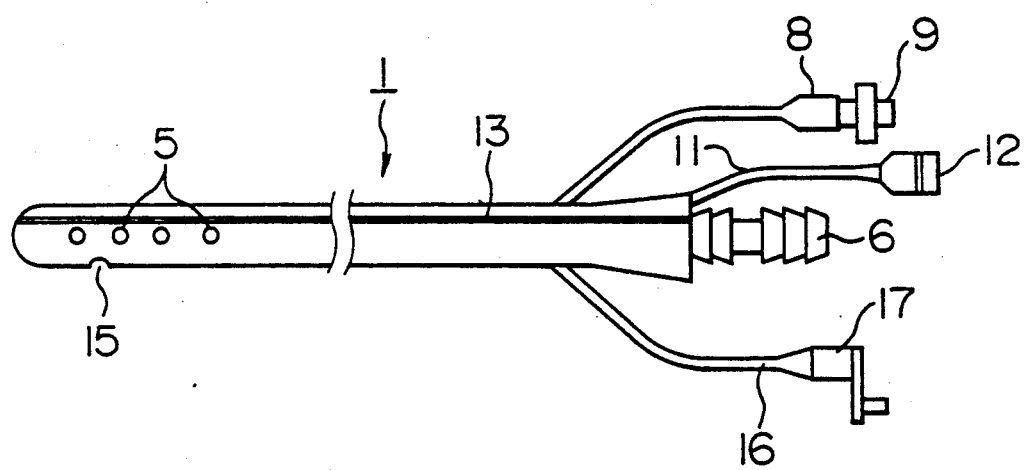
FIG. 2A shows another embodiment of the present invention.
Figure 2B:
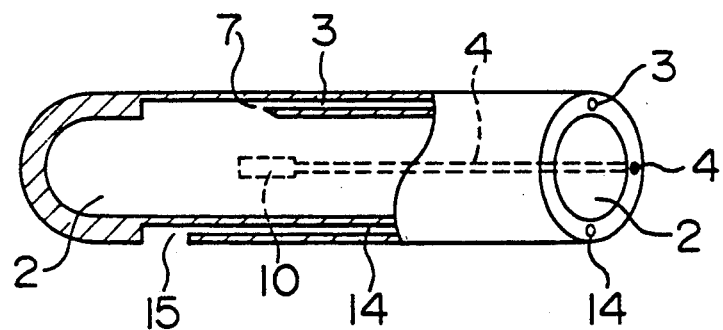
FIG. 2B is an enlarged and cross-sectional view of the tip portion shown in FIG. 2A.

FIG. 2A and 2B show another embodiment of the present invention. In addition to the drainage function with sampling and the temperature measuring function, the catheter also has a pressure-measuring function. In addition to the functions shown in FIG. 1A, this monitoring catheter (1) is provided with second auxiliary tube (14) within the wall of the main tube (2). The second auxiliary tube (14) has a bore (15) towards the outer surface of the body of the main tube (2) near the tip portion of the catheter (1). At the same time, the second auxiliary tube is branched from the main tube near the rear end of the body of the catheter. At the branched tube (16), connecting part (17) with a means for opening-closing is mounted to display or record the measurement data by connecting with a monitor. By the foregoing construction, the functions to measure and transfer the pressure in a specific region in the body cavity can be imparted to the catheter.

Figure 3A:
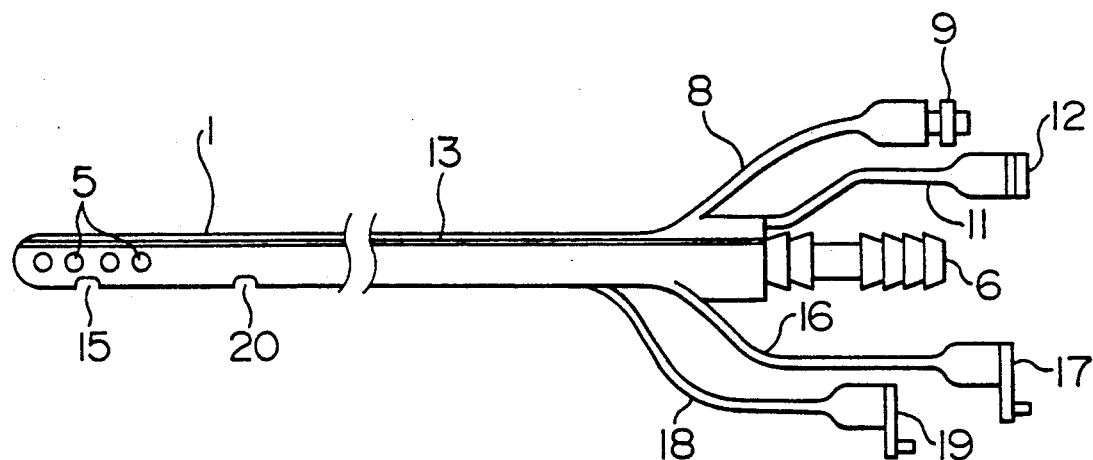
FIG. 3A shows a further embodiment of the present invention, FIGS. 3B and 3C each show an enlarged and cross-sectional view of the tip portion shown in FIG. 3A.
Figure 3B:
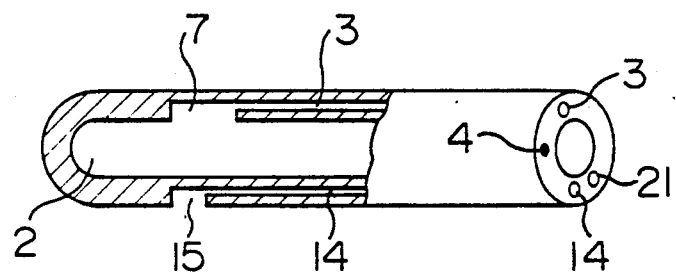
Figure 3C:
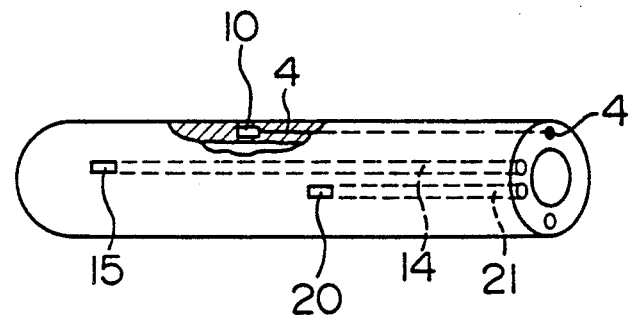

FIGS. 3A, 3B and 3C a further embodiment of the present invention, having the function to measure pressures at two different regions, in addition to the drainage function with sampling and the temperature-measuring function.

That is, this embodiment shows a monitoring catheter further equipped with the third auxiliary tube (21) having a function to measure blood pressure at a different region located within the wall of the main tube (2), in addition to the construction shown in FIG. 2B.

The third auxiliary tube (21) is located within the wall of the main tube (2) at the place apart from the second auxiliary tube (14). The third auxiliary tube (21) has a bore (20) towards the outer surface of the body of the main tube (2) and at the same time, the second auxiliary tube is branched from the main tube near the rear end of the body of the catheter. At the branched tube (18), connecting part (19) with a means for opening-closing is mounted to display or record the measurement data by connecting with a monitor. By further providing the third auxiliary tube (21), this monitoring catheter has the function to measure and transfer the pressures in two different regions in the body cavity.

The bore (15) of the second auxiliary tube is located near the rear end of the body of the catheter (1). The bore (20) of the third auxiliary tube is located at a distance of 5 to 70 cm at the rear end from the bore (15). When the distance is less than 5 cm, the positions of both bores are so close that it is medically insignificant to the pressure in two regions at the same time. Also when the distance exceeds 70 cm, it is clinically meaningless.

It is, of course, possible to supply a liquid drug through the second and third auxiliary tubes for pressure measurement. In this case, the liquid drug can be more advantageously supplied without being retained, since the bores are open towards the outer surface of the catheter (1).

Figure 4:
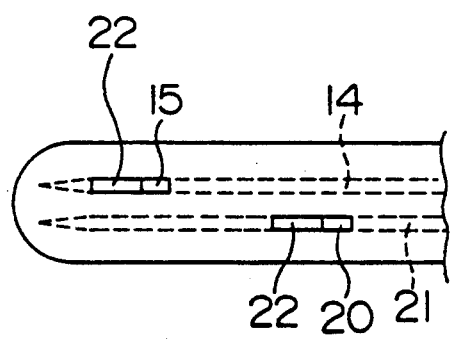
FIGS. 4 and 5 show constructions of the tip portions of medical catheter which are still further embodiments of the present invention.
Figure 5:
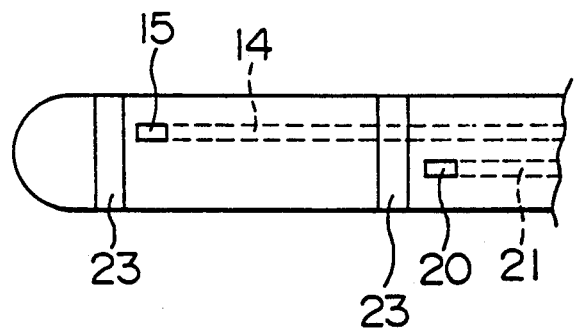

As is illustratively shown in FIG. 4, in order to detect the positions of the bores (15) and (20), X ray-impermeable material (22) may also be incorporated at the tip portion ahead of the bores (15) and (20) of the second auxiliary tube and third auxiliary tube, upon inserting into the body. As examples of the X ray-impermeable material (22), an X ray-impermeable material such as barium sulfate, etc. may be kneaded with an adhesive or a metal wire or the like may be embedded, but the X ray-impermeable material is not limited to these examples. As shown in FIG. 5, it is also effective to mount a metal ring (23) around the bores (15) and (20). For such a material, stainless or the like is advantageously used.

In addition to the secondary and third auxiliary tubes, it is also possible to provide a plurality of passageways for pressure measurement. Such an embodiment is also included in the present invention.

By the use of the monitoring catheter for medical use in accordance with the present invention, secretions when kept stuck can be readily discharged. Furthermore, if necessary and desired, a drug solution can be infused and washing can be made so that it is possible to perform measurement of a temperature comfortably by keeping the catheter inserted over a relatively long period of time. Not only during operation but also after operation or treatment, diagnosis and control can be made smoothly. Moreover, the catheter also has the function to measure pressure. Therefore, information on the body temperature can be obtained in more detail and is advantageous for postoperative observation, diagnosis and control. These functions are imparted to a single catheter so that pains given to the patient are minimized and handling is easy. Therefore, the present invention can contribute to keeping the patient's condition more stable by performing temperature control during, e.g., cardiac operation, and postoperative temperature control when the catheter is kept inserted. Furthermore by applying the catheter to respiration control through the pressure measurement, the present invention can greatly contribute to postoperative observation, control and diagnosis.

In particular, by providing two or more pressure monitoring lines as in the present invention, pressures at two different regions can be measured at the same time. Accordingly, by simultaneously measuring two pressures in, e.g., esophagus and stomach which are highly correlated to the internal thoracic pressure, respiratory work done which could have been hitherto determined only with difficulty can be quantitatively determined. It is also possible to determine adequate conditions when an artificial respirator is used. This is extremely useful for respiration control, etc., for example, of after cardiac peration.

What is claimed is:

1. A monitoring catheter for medical use comprising,
    a main tube for discharge path of body fluids, etc.,
    a first auxiliary tube for air flow which is located within the wall of said main tube,
    second and third auxiliary tubes which respectively form a passageway for a liquid drug infusion or for measuring pressure and which are located within the wall of said main tube,
    a lead for measuring temperature which is located in a fixed position within the wall of said main tube,
    said main tube having a plurality of bores on the wall near the tip portion thereof,
    a tip portion of said first auxiliary tube being open towards the inner surface of said main tube,
    said second auxiliary tube having an opening on the outer surface of said body of said main tube located near a tip portion of said main tube,
    said third auxiliary tube having an opening toward the outer surface of said catheter at a distance of about 5 to 70 cm from said opening of said second auxiliary tube in a direction toward a rear of said main tube, and
    a tip portion of the lead being located near a tip portion of the catheter and being provided with a temperature sensor.

2. A monitoring catheter for medical use as claimed in claim 1, wherein said main tube contains a connecting portion for connecting with a container for drainage capture at the rear end of said main tube.

3. A monitoring catheter for medical use as claimed in claim 1, wherein said first auxiliary tube is branched from said main tube near the rear end of said catheter and has a filter at the rear end thereof.

4. A monitoring catheter for medical use as claimed in claim 1, wherein at least one of said second and third auxiliary tubes is branched from said main tube near the rear end of said catheter and has a connecting portion having a means for opening-closing at the rear end thereof.

5. A monitoring catheter for medical use as claimed in claim 1, wherein said lead is branched from said main tube near the rear end of said catheter and has a connecting portion at the rear end thereof.

* * * * *